United States Patent [19]

Beatty

[11] Patent Number: 4,968,604
[45] Date of Patent: Nov. 6, 1990

[54] METHOD AND TEST KIT FOR DETECTION OF ANTIBODIES

[75] Inventor: Shannon M. Beatty, Edmonds, Wash.
[73] Assignee: NeoRx Corporation, Seattle, Wash.
[21] Appl. No.: 383,779
[22] Filed: Jul. 20, 1989
[51] Int. Cl.$^5$ .................. G01N 33/535; G01N 33/545
[52] U.S. Cl. .......................................... 435/7; 422/56; 422/61; 435/805; 436/530; 436/531; 436/808; 436/809; 436/810
[58] Field of Search ................... 435/7, 805; 436/530, 436/531, 808–810; 422/56, 61

[56] References Cited

U.S. PATENT DOCUMENTS

| | | | |
|---|---|---|---|
| 2,278,339 | 1/1940 | Vollmer | 436/809 X |
| 4,157,895 | 6/1979 | Finlay et al. | 436/809 X |
| 4,654,310 | 3/1987 | Ly | 435/805 X |

OTHER PUBLICATIONS

Schroff et al., "Human Anti–Murine Immunoglobulin Responses in Patients Receiving Monoclonal Antibody Therapy", Cancer Res. 45(1985), 879–885.

*Primary Examiner*—Christine Nucker
*Attorney, Agent, or Firm*—Stoel, Rives, Boley, Jones & Grey

[57] ABSTRACT

Assay methods and test kits for detection of antibodies having specificities for a variety of determinants in patient samples are disclosed. The assay is especially suitable for use in evaluating patients for their suitability to receive diagnostic and therapeutic immunoconjugates comprising immunoglobulin constituents derived, at least in part, from a non-human source. The assay methods and test kits utilize a target substance (e.g., immunoglobulin) which has substantially the same binding characteristics as a portion of the immunoconjugate proposed for in vivo administration. A plurality of target substance densities are used for assaying each patient specimen to provide an indication of both the level and relative affinity of circulating antibody capable of binding to the immunoconjugate proposed for treatment. According to preferred embodiments, the assay utilizes a dipstick or test strip format wherein multiple densities of a target substance are bound to a support medium in a predetermined spatial relationship, preferably in a side-by-side relationship.

28 Claims, 2 Drawing Sheets

METHOD AND TEST KIT FOR DETECTION OF ANTIBODIES

TECHNICAL FIELD

The present invention relates generally to improved methods and test kits for detection of antibodies in a test specimen such as patient serum.

BACKGROUND ART

Agents that are effective in killing neoplastic and other diseased or abnormal cells generally cannot be administered to a patient in therapeutically effective doses, because they also exert cytotoxic effects on normal cells. Therapeutic protocols for treating cancer and other disorders using cytotoxic agents such as toxins, drugs, radioisotopes and the like, are generally limited by the toxicity of the cytotoxic agent to normal cells and tissues. Efforts have therefore been directed to linking cytotoxic therapeutic agents to carriers, such as antibodies, which have an affinity and specificity for certain target tissues, cells and antigens.

Recent research efforts in the field of tumor immunology have identified antibodies to antigenic determinants expressed preferentially on tumor cells. Such antibodies may be employed as carriers for cytotoxic agents to provide selective delivery of cytotoxic agents to target tissues. Antibodies, fragments thereof and the like have also been utilized as carriers for diagnostic agents such as diagnostic radioisotopes, to provide highly selective delivery of the diagnostic agent to the target tissue, thereby providing enhanced imaging properties. In vivo administration of diagnostic and therapeutic immunoconjugates comprising an effector moiety exhibiting diagnostic or therapeutic properties and a carrier moiety exhibiting specificity and affinity for target tissues, cells, antigens, or the like are believed to be of tremendous potential in diagnosis and treatment of cancer and a variety of other diseases.

Development of techniques for generating monoclonal antibodies having specificity for a single epitope has further expanded the potential for immunoconjugates as in vivo diagnostic and therapeutic agents. One of the problems associated with in vivo administration of immunoconjugates to patients for diagnostic or therapeutic purposes is that the immunoconjugate itself, or some portion thereof, may stimulate a humoral immune response in the patient. This problem may arise frequently, since antibodies raised in non-human species are typically employed in diagnostic and therapeutic immunoconjugates for in vivo administration in humans. Stimulation of a humoral immune response will result in production of serum antiglobulin and may result in formation of immune complexes comprising serum antiglobulin and the immunoconjugate administered. Formation of immune complexes may seriously hamper the efficacy of the product, and may, in some cases, pose a serious health hazard to the patient.

Formation of immune complexes comprising the immunoconjugate, or a portion thereof, bound to circulating antiglobulin as a result of in vivo administration of diagnostic or therapeutic immunoconjugates may affect the biodistribution and clearance rate of the immunoconjugates. In general, formation of immune complexes reduces the amount of immunoconjugate available for diagnostic or therapeutic purposes and results in retention of the administered immunoconjugate in non-target tissues. With respect to diagnostic immunoconjugates, stimulation of a humoral immune response and formation of circulating immune complexes is detrimental primarily because it disperses the diagnostic agent, and thereby reduces imaging clarity. For therapeutic immunoconjugates, however, the detrimental effects of in vivo immunoconjugate administration may be considerably more serious, since formation of circulating immune complexes comprising cytotoxic agents not only reduces the cytotoxic effect of the immunoconjugate on the target cell population, but it localizes cytotoxic agents in non-target tissues such as the liver and kidneys, and these tissues may be seriously damaged.

Where the carrier moiety of the immunoconjugate is derived from a species different from that of the patient, the probability of stimulating antiglobulin production in the patient is very high. In efforts to reduce the immunogenicity of immunoconjugates comprising carrier moieties derived from non-human sources, antibody fragments have been used to quantitatively reduce the total amount of foreign protein, while providing the same or increased levels of binding capacity. Use of antibody fragments such as Fab, Fab', F(ab')$_2$, and the like is well known in the art. In addition, chimeric antibodies have been developed in efforts to reduce the immunogenicity of carrier moieties derived from non-human sources. Chimeric antibodies may comprise specificity determining regions derived from non-human sources, while other portions of the antibody, such as the constant regions, are of human origin. Immunogenicity of conjugates comprising non-human antibody constituents, however, remains a serious problem and limits the diagnostic and therapeutic application of immunoconjugates. Anti-allotype reactivity to the human constant domains of chimeric antibodies may also affect the efficacy of immunoconjugates comprising chimeric carrier moieties Conventional immunoassays for detecting antibodies and antigens include enzyme immunoassays such as the ELISA (enzyme-linked immunosorbent assay) protocol, radioimmunoassays such as the RIA-immunoprecipitation assay, and immunofluorescence protocols. Typically, a predetermined quantity of antigen (or antibody) is adsorbed on a solid phase, protein binding surface. The test sample to be assayed for antibodies (antigens) is then contacted to the surface having antigen (antibody) bound thereto, and antibodies (antigens) in the test sample bind to the immobilized antigen (antibody). Radioactive or enzyme-labeled immunoglobulin probes are then contacted to the surface and bind to the immobilized antibodies (antigens). The amount of labeled probe bound to the solid support can be quantitated and is indicative of the antibody (antigen) concentration in the test sample.

ELISA protocols typically involve multiple microassays utilizing several dilutions of human serum and a single target antigen (antibody) concentration. Microtiter plates are typically used for performing the multiple microassays necessary to detect the presence of antibody (antigen). ELISA protocols require extensive handling and manipulation of samples and reagents, which may substantially reduce the accuracy of the assay results. In fact, coefficients of variance of up to 25% and 30% are not unusual for ELISA results. This level of accuracy may be unacceptable for many applications, and particularly for applications involving evaluation of patients for therapeutic protocols utilizing immunoconjugates comprising radionuclides, toxins and the like. In addition, spectrophotometric equipment such as a microplate reader is effectively required for accurate analysis of the assay results, since manual analysis significantly reduces accuracy of the assay results. Such equipment requires a substantial capital investment, which may not be practicable unless assays are performed on a relatively large, commercial scale.

Disadvantages of using radioimmunoassay procedures include the necessity of extensive sample manipulations, including multiple dilutions, incubations and washing steps. In addition, a potentially hazardous radioisotope such as $^{125}I$ is employed. Processing samples according to a radioimmunoassay protocol consumes at least several hours, and requires relatively complex laboratory equipment and skilled technicians. Immunofluorescent staining generally provides an accurate indication of specificity, and it permits visualization of the antigen-antibody reaction. Immunofluorescence methodologies, however, are time consuming and difficult to perform on a large scale. Moreover, analysis of immunofluorescence assay results requires the analytical judgment of experienced technicians.

SUMMARY OF THE INVENTION

The present invention is directed to methods and test kits for detecting the presence of antibodies, and, more specifically, antibodies capable of binding to constituents of in vivo diagnostic or therapeutic substances. The assay is especially suitable for use in evaluating the suitability of human patients to receive diagnostic and therapeutic immunoconjugates comprising antibodies or fragments thereof derived, at least in part, from a non-human source. According to preferred embodiments, the assay may be packaged in test kit form, and it preferably employs a dipstick or test strip format.

The term "antibody," as used in this disclosure, comprehends immunoglobulins having specificity for a variety of determinants. Immunoglobulins, toxins, lectins, carbohydrates, and other substances may elicit immunogenic responses when administered to a patient, and production of antibodies to a variety of substances may be detected and monitored according to methods of the present invention. While the disclosure of the present invention refers to preferred embodiments for detecting antiglobulins capable of binding to target immunoglobulins, it is recognized that antibodies to a variety of target substances may be detected using the methods and test kits of the present invention. Similarly, although the disclosure of the present invention is directed to detecting and/or monitoring antiglobulin production in humans in connection with in vivo administration of diagnostic or therapeutic products, it will be recognized that the methodology may be adapted for use in other applications and species as well.

The efficacy and safety of therapeutic and diagnostic immunoconjugate treatment protocols appears to be correlated with the specificity of circulating antibodies in particular patients, and not with the presence or level of non-specific circulating antibodies. The presence of antibodies capable of binding to an immunoconjugate proposed for in vivo administration may seriously undermine the efficacy and safety of the diagnostic or treatment protocol. Antibodies capable of binding to the immunoconjugate proposed for treatment should be assayed prior to in vivo administration of diagnostic or therapeutic immunoconjugates.

Typically, immunoassays are performed using multiple dilutions of a test specimen and a single concentration (density) of target substance (immunoglobulin). An important feature of the antibody assay of the present invention is that it utilizes a plurality of target substance densities to provide a plurality of corresponding patient specimen test regions. According to a preferred embodiment, the target substance is an immunoglobulin which is substantially the same as, or is functionally equivalent to, the carrier moiety of an immunoconjugate proposed for in vivo administration. These aspects of the assay methods of the present invention may be incorporated in a variety of immunoassay protocols. For example, radioimmunoassay and enzyme immunoassay protocols may be performed and the results analyzed using conventional techniques and reagents, but utilizing multiple densities of target substance to provide corresponding multiple patient specimen test regions according to the methods of the present invention.

Assay results indicate not only the presence of antibodies capable of binding to the target substance, but also the relative affinity of circulating antibodies for the target. In general, lower affinity antibodies bind better to higher density target areas than higher affinity antibodies, while higher affinity antibodies bind better to lower density target areas than lower affinity antibodies. Thus, the level of antibodies having specificity for the target substance can be determined by quantifying the amount of labeled probe immobilized on the support, while the relative affinity of the antibodies can be determined by the distribution of labeled probe on higher or lower density target areas. Although identification of the specificity of circulating antibodies is of primary importance, information relating to the affinity of circulating antibodies is also clinically useful.

The assay test kit preferably employs a dipstick or test strip format utilizing a solid support medium capable of binding proteins or other target substances. Multiple concentrations of the target substance are bound to the test strip in a predetermined spatial relationship.

The test strip is exposed to the patient test specimen of interest, generally patient serum or a dilution thereof, to permit antibodies present in the patient specimen to bind to target substances immobilized on the test strip. After a suitable incubation period, test strips are thoroughly washed to remove unbound constituents. The test strip is then contacted to a labeled probe capable of binding to the antibody of interest. Enzyme-labeled probes are preferred for use with test strips according to the present invention Assay results may be visualized by further incubation of the test strips with a chromogenic substrate. A preprinted color gradient chart is preferably provided for analysis of the patient antibody level by comparison of the multiple regions of the test strip to the color chart. Assay results yield a reliable indication of the level of antibody capable of binding to the target substance, as well as the relative affinity of the antibody for the target substance.

Controls are preferably run in parallel with the patient samples to confirm that the reagents and the test protocol operated in accordance with predictable and acceptable standards. A suitable control may be provided by a reference or standard specimen, generally a serum sample, that is exposed to a test strip, and processed in parallel with the patient specimen so that the experimental conditions for the control and patient specimens are substantially identical. If the control test strip does not produce the anticipated results, the assay procedure should be repeated and verified.

According to an especially preferred embodiment of the test kit of the present invention employing a test strip or dipstick format, the test strip itself may include control regions. Control regions having a predetermined density of target substance bound thereto, and additionally having a predetermined quantity of antibody bound to the immobilized target substance, may be arranged on the test strip. Both high and low control regions are preferably provided. The low control region has a relatively low level of bound antibody and validates the test protocol, while the high control region has a relatively high level of bound antibody and may serve to provide a benchmark warning or safety level.

The antibody assay of the present invention may be performed without extensive manipulations of test samples and reagents, and it provides accurate results in a relatively short time period. Since the assay does not require complex equipment or technical skill to perform the assay or accurately analyze the results, it provides an assay for detection of antiglobulin which provides accurate results at virtually any testing site at a reduced cost compared to commercially available assay procedures.

BRIEF DESCRIPTION OF THE DRAWINGS

The above-mentioned and additional features of the present invention and the manner of obtaining them will become apparent, and the invention will be best understood by reference to the following more detailed description read in conjunction with the accompanying drawings, in which.

Figure 1:
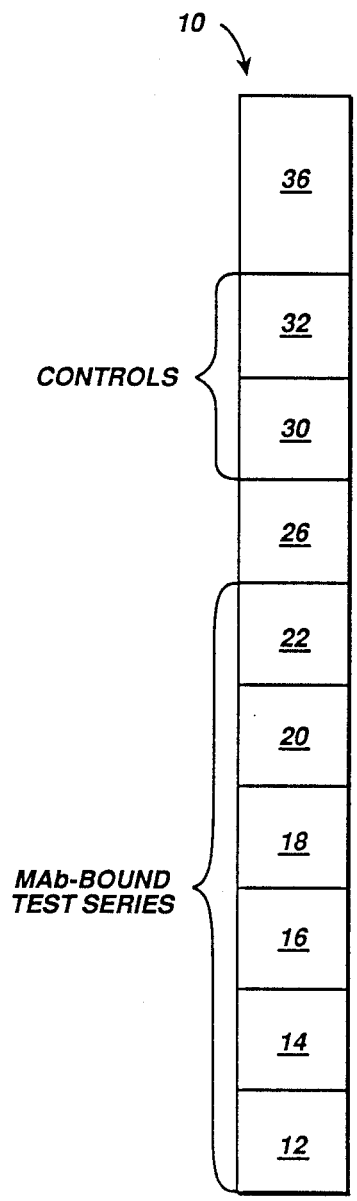
FIG. 1 illustrates an antibody assay test strip according to the present invention, including a control portion with high and low control test regions, and a plurality of test regions having various concentrations of target immunoglobulin bound thereto.

Test Strip I: low titer, low affinity antiglobulin;
Test Strip II: low titer, high affinity antiglobulin;
Test Strip III: high titer, low affinity antiglobulin; and
Test Strip IV: high titer, high affinity antiglobulin.

BEST MODE FOR CARRYING OUT THE INVENTION

As noted above, the assay methods and test kits of the present invention may be used for detecting the presence of antibodies having specificities for a variety of determinants. The detailed description set forth below relates specifically to detection of antiglobulin capable of binding to target immunoglobulins having binding characteristics similar to immunoglobulins or immunoglobulin fragments incorporated in diagnostic or therapeutic immunconjugates, but the methods and test kits of the present invention are not limited to this application.

One important application of the methods and test kits of the present invention is evaluation of patients for their suitability to receive diagnostic or therapeutic immunoconjugates. In connection with this clinical application, another important aspect of the present invention is that the target immunoglobulin has binding characteristics substantially similar to and preferably functionally equivalent to an immunoconjugate proposed for in vivo administration. In many instances, the target substance will be a monoclonal antibody (MAb) or fragment thereof, which serves as the carrier moiety for an immunoconjugate proposed for in vivo administration. It is especially preferred that specificity determining regions of the target immunoglobulin are identical to the corresponding specificity determining regions of the immunoconjugate carrier moiety. For example, if an immunoconjugate being considered for treatment includes a carrier moiety comprising a murine antibody or fragment thereof, it is important that the target immunoglobulin has substantially the same binding characteristics as the murine antibody employed in the immunoconjugate. Target immunoglobulin comprising non-specific murine immunoglobulin would not be suitable. This feature of the assay of the present invention may also be utilized in connection with conventional immunoassay protocols.

The methods and test kits of the present invention may be used to monitor patients for immune responses after in vivo administration of diagnostic or therapeutic immunoconjugates. If a diagnostic or therapeutic protocol requires multiple administrations of the same or different immunoconjugates, an assay should be performed prior to each in vivo administration. In some cases, patient evaluation for initial or continued treatment with an immunoconjugate may require multiple assays to assess the patient's humoral immune response to different components of the immunoconjugate. Administration of certain toxins, for example, may elicit antibody production. Evaluation of immunoconjugates comprising an immunoglobulin component and a toxin component may therefore require independent assay of patient test specimens for antibodies to both the immunoglobulin and the toxin component of the immunoconjugate.

The assay methods and test kits of the present invention preferably utilize a test strip or dipstick format wherein target immunoglobulin is bound to a solid support medium capable of binding proteins. Suitable solid support media, such as nitrocellulose paper, diazo paper, glass fiber paper, and the like, are well known in the art. Techniques for binding target immunoglobulin to such solid support media are also well known. Target immunoglobulin is preferably covalently bound to the solid support medium.

Preferred embodiments of the methods and test kits of the present invention utilize a test strip having a plurality of densities of the target immunoglobulin immobilized on the test strip in a predetermined spatial relationship. FIG. 1 illustrates a preferred test strip format according to the present invention. Test strip 10 comprises a solid support medium having patient specimen test regions 12, 34, 16, 18, 20 and 22 arranged in side-by-side relationship. Each of the patient specimen test regions has a predetermined density of target immunoglobulin bound thereto, and each test region is preferably visibly delineated so that assay results for the multiple test regions are identifiable. Although six patient specimen test regions are illustrated, from about two to about ten or more patient specimen test regions arranged in side-by-side relationship may be suitable for various applications.

Patient specimen test regions are preferably arranged in ascending or descending order of target immunoglobulin density. For example, test region 12 may have 0.01 ng MAb bound thereto; test region 14, 0.1 ng MAb; test region 16, 1.0 ng MAb; test region 18, 10 ng MAb; test region 20, 100 ng MAb; and test region 22, 1000 ng MAb. The gradations in target immunoglobulin concentration may, of course, vary with different target immunoglobulins exhibiting various anticipated antiglobulin binding characteristics Test strip 10 and test regions 12-22 are provided in a test strip or dipstick format to facilitate contacting the patient specimen test regions to patient specimens and the necessary assay reagents. Handling region 26, having no immunoglobulin bound thereto, is preferably provided in proximity to the innermost patient specimen test region 22 to facilitate handling and manipulation of the test strip. A visible marker may be provided to clearly differentiate the patient specimen portions of the test strip from the handling region.

Control regions 30 and 32 are preferably incorporated directly on test strip 10 so that a single test strip provides both patient specimen assay results and protocol verification. Control regions 30 and 32 have a predetermined density of the target immunoglobulin bound thereto, and additionally have a predetermined quantity of antiglobulin bound to the immobilized target immunoglobulin. When the target immunoglobulin comprises a murine MAb or fragment, for example, human anti-mouse immunoglobulin reactive with the target murine MAb would be preferred for use in control regions 30 and 32. Since human anti-mouse immunoglobulin is generally unavailable, however, antiglobulin bound to the control regions may be derived from a concentrated fraction of immune human serum immunoglobulin, preferably IgG, which is reactive with a wide range of target immunoglobulins to provide a positive control.

Both high and low control regions are preferably provided. For example, control region 30 may represent the low control, which has a relatively low density of bound antiglobulin The low control region verifies the experimental reagents and protocol for that particular assay. Control region 32 may represent the high control, which has a relatively high density of antiglobulin and provides a benchmark indication of an elevated level of antiglobulin capable of binding to the target immunoglobulin. Additional control regions may, of course, be provided as desired. Handling area 36 having no protein bound thereto may be provided in proximity to the control regions for ease of handling and manipulation A specimen comprising bodily fluids from the patient being evaluated for diagnostic or therapeutic immunoconjugate treatment is used as the patient test specimen. Serum samples are preferred and may be prepared using conventional techniques. Patient serum may be diluted as necessary (generally about 1/10) with an appropriate diluent. A test strip of the type described above is contacted to the patient specimen for a time interval sufficient to permit antiglobulin having specificity for the target immunoglobulin to bind to the immobilized target immunoglobulin, if it is present in the patient specimen. Antiglobulin binding incubation periods of from about 20 minutes to about 90 minutes, and preferably about 60 minutes, are generally suitable at room temperature. If control regions having target immunoglobulin and a predetermined quantity of antiglobulin bound thereto are incorporated on the test strip, the control regions are not contacted to the patient specimen. After incubation with the patient specimen, the test strip is thoroughly washed to remove all constituents which have not bound to the test regions.

The test strip is subsequently contacted to a labeled probe reagent capable of binding to antiglobulin. The labeled probe binds to antiglobulin immobilized on the test strip, and thus indicates the presence of immune complexes formed between antiglobulin from the patient specimen and the target immunoglobulin. Enzyme-labeled probes are preferred for use with the solid phase test strip of the present invention. Incubation periods of about 10 minutes to about 60 minutes, and preferably about 30 minutes, are suitable Both patient specimen regions and control regions are contacted to the labeled probe reagent.

The labeled probe is preferably derived from the same species as the target immunoglobulin, to reduce the incidence of cross-reaction with target immunoglobulin, which would distort the assay results. One preferred enzyme-labeled probe for use with target immunoglobulins derived, at least in part, from murine sources, is horseradish-peroxidase (HRPO)-labeled $F(ab')_2$ mouse antihuman IgG and IgM that is diluted in PBS-Tween (Dulbecco's PBS without $Ca++$, $Mg++$, containing 0.5% Tween 20). After exposure to the labeled probe for a suitable incubation period, test strips are thoroughly washed to remove all unbound labeled probe reagent.

When an enzyme-labeled probe is used according to preferred embodiments of the present invention, the test strip is thereafter contacted to a chromogenic substrate which reacts with the enzyme to produce a visible colored product. Suitable chromogenic substrates such as ABTS (2,2'-azino-bis (3-ethylbenzthiazoline-6-sulfonic acid), TMB (3,3',5,5'tetramethylbenzidine), DAB (diaminobenzidine), OPD (o-phenylene diamine), and the like, are well known in the art. TMB and OPD are especially preferred chromogenic substrates, since they precipitate well on solid support media, and they do not exhibit toxic, carcinogenic or mutagenic properties. OPD requires use of a stopping agent, such as hydrochloric or sulfuric acid, to terminate and "freeze" colored product formation Incubation periods of from about 10 minutes to about 30 minutes, and preferably about 15 to 20 minutes with chromogenic substrates are generally suitable. Following a suitable incubation period with the chromogenic substrate and treatment with a stopping agent, if necessary, the test strip is thoroughly washed to remove all unbound substrate material.

To facilitate analysis of the antiglobulin assay results, preferred embodiments of the test kit of the present invention utilizing an enzyme-labeled probe preferably include a pre-printed color gradient chart. The color intensity of various patient specimen test regions indicates the level of antiglobulin having specificity for the target immunoglobulin. Color gradient charts may be standardized as necessary for various assay protocols and target immunoglobulins. Although it may be possible to standardize color gradient charts for assays involving different target immunoglobulins, it is preferred to provide a color gradient chart corresponding to each target immunoglobulin.

When the test strip comprises only patient specimen test regions and does not incorporate control test regions, designated control test strips are preferably run in parallel with patient specimen test strips to verify the efficacy of the protocol. Controls may be run by contacting standard test strips according to the present invention having a plurality of test regions arranged thereon to a control specimen, and processing the control test strips in parallel with the patient specimen test strips. A control specimen containing a known or quantifiable amount of antiglobulin derived from the same species as the test specimen is preferred. The capability of antiglobulin in the control specimen to bind to the target immunoglobulin must also be predetermined. If the control test strips do not react in a predictable manner, the assay protocol and reagents should be re-examined and the patient specimen assay should be repeated.

Figure 2:
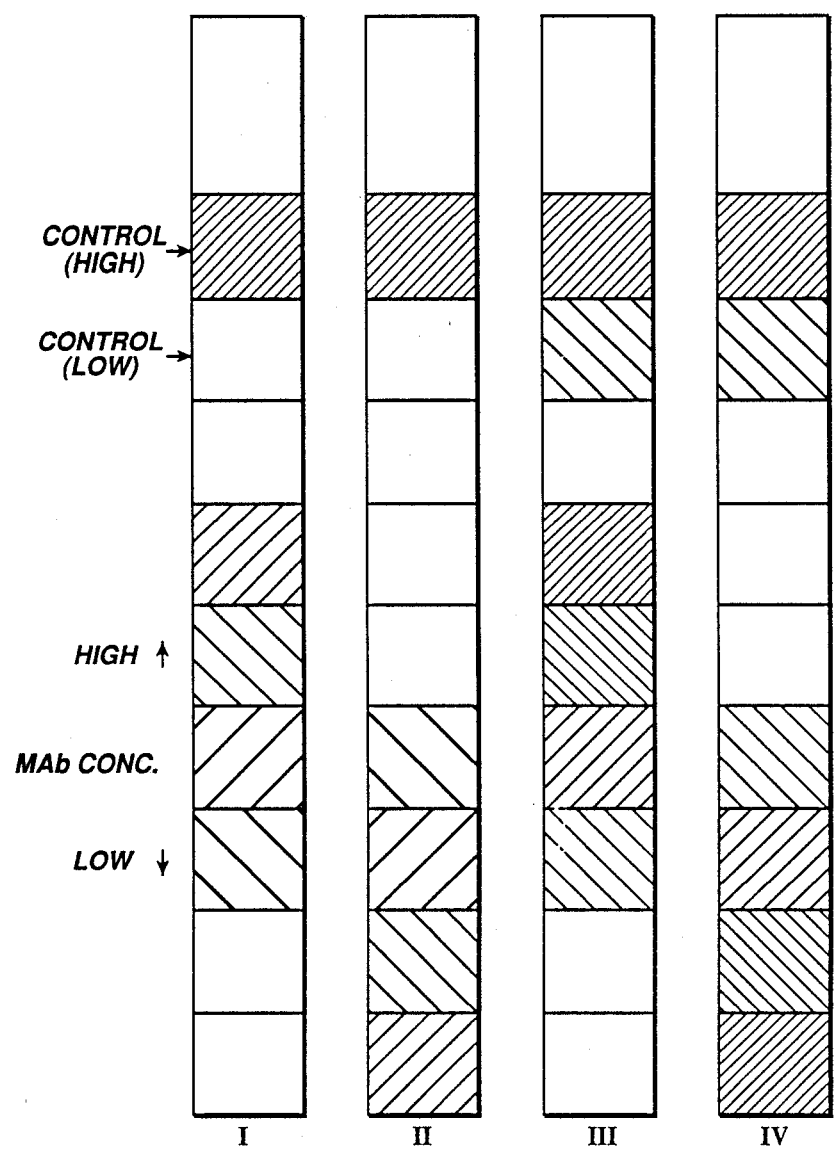
FIG. 2 illustrates four positive antiglobulin assay results using test strips of the type described with reference to FIG. 1. Test strips I–IV illustrate the following results.

FIG. 2 schematically illustrates four positive antiglobulin assay results obtained utilizing the immunoassay methods of the present invention and test strips of the type illustrated in FIG. 1. The target immunoglobulin densities are arranged in ascending order from the terminal test region (shown as 12 in FIG. 1), and the high control is the upper control region (shown as 32 in FIG. 1). In each of the test strips I-IV, the high control has a relatively high density color, while the low control has a relatively low density color. The high control provides a benchmark of analytical significance, and patient specimen test regions which approach the color density of the high control should be carefully evaluated. If color development on the low control is different from that indicated as standard, the test should be repeated, since the unpredictable results indicate defective reagents, inaccurate test procedures, or the like.

Test strips I and II are exemplary of low titer antiglobulin patient specimens, as evidenced by their relatively low density color reaction, while test strips III and IV are exemplary of higher titer antiglobulin samples, as evidenced by their relatively high density color reaction The relative affinity of antiglobulin having specificity for the target immunoglobulin is also indicated by the assay results illustrated in FIG. 2. For example, test strips I and III illustrate assay results indicating antiglobulin specific for the target immunoglobulin which has relatively low affinity, since binding to test regions of higher target immunoglobulin concentration predominates. Test strips II and IV illustrate assay results indicating antiglobulin specific for target immunoglobulin which has a relatively high affinity, since binding to test regions having lower target antibody concentration predominates. In general, lower affinity antiglobulins bind better to higher density target immunoglobulin areas, while higher affinity antiglobulins bind better to lower density target immunoglobulin areas.

The test kit of the present invention, in its simplest form, comprises a test strip having a plurality of densities of target immunoglobulin bound thereto in a predetermined spatial relationship, preferably in side-by-side relationship. Additionally, the test kit preferably comprises a pre-printed color gradient chart of the type described above to facilitate analysis of the assay results. One or more of the assay reagents, such as the labeled probe and the chromogenic substrate, are also preferably provided in the test kit. Reagents may be provided in suitable form and concentration for use directly in the assay, provided that their activity does not deteriorate due to storage or other conditions. Reagents may alternatively be provided in a preserved form, along with solutions necessary for reconstitution. Suitable vessels for carrying out the incubation procedures may also be provided. The test kit is designed for use in conjunction with a diagnostic or therapeutic immunoconjugate protocol, and may be provided in connection with or packaged with the diagnostic or therapeutic immunoconjugate product intended for in vivo administration.

The immunoassay methods and test kits of the present invention utilizing a dipstick or test strip format provide accurate assay results in a relatively short time period of about two to four hours or less. Since performance of the assay and analysis of the assay results do not require complex laboratory equipment, the assay may be performed at virtually any testing site. In addition, the costs involved with the assay methods and test kits of the present invention may be significantly less than many commercially available assay procedures.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

I claim:

1. A support medium having a plurality of densities of a target substance bound thereto in a predetermined spatial relationship, wherein said target substance bas binding characteristics similar to binding characteristics of a diagnostic or therapeutic substance proposed for in vivo administration to a patient to permit evaluation of said patient's response to said diagnostic or therapeutic substance.

2. A support medium according to claim 1, wherein said target substance is covalently bound to said support medium.

3. A support medium according to claim 1, wherein said predetermined spatial relationship is a side-by-side relationship.

4. A support medium according to claim 3, wherein said plurality of densities of said target substance provides a plurality of patient specimen test regions arranged in ascending order of density.

5. A support medium according to claim 1, wherein said target substance is a target immunoglobulin, and said target immunoglobulin has binding characteristics similar to binding characteristics of a carrier moiety of said immunoconjugate proposed for in vivo administration.

6. A support medium according to claim 5, wherein said target immunoglobulin and said carrier moiety are derived, at least in part, from the same species of origin.

7. A support medium according to claim 5, wherein specificity determining regions of said target immunoglobulin are identical to corresponding specificity determining regions of said carrier moiety.

8. A support medium according to claim 5, wherein said target immunoglobulin and said carrier moiety are derived, at least in part, from a murine source.

9. A support medium according to claim 5, wherein said target immunoglobulin and said carrier moiety comprise a monoclonal antibody or a fragment thereof.

10. A support medium according to claim 1, wherein said diagnostic or therapeutic substance is an immunoconjugate.

11. A support medium according to claim 10, wherein said target substance has binding characteristics similar to an effector moiety of said immunoconjugate proposed for in vivo administration.

12. A support medium according to claim 11, wherein said effector moiety of said immunoconjugate comprises a toxin.

13. A support medium according to claim 1, additionally comprising at least one control region provided on said support medium, said control region having a predetermined density of said target substance bound thereto, and additionally having a predetermined density of antibody bound to said target substance.

14. A support medium according to claim 13, comprising a high control region and a low control region provided on said support medium, said high control region having a relatively high density of antibody immobilized thereon, and said low control region having a relatively low density of antibody immobilized thereon.

15. A support medium according to claim 14, wherein said antibody bound to said target substance at said control regions comprises immune human serum immunoglobulins.

16. An assay kit comprising a support medium according to claim 1, and a vial containing an enzyme-labeled probe reagent capable of binding to antibodies that bind to said target substance.

17. An assay kit according to claim 16, wherein said enzyme-labeled probe reagent comprise HRPO-labeled F(ab')$_2$ mouse anti-human IgG.

18. An assay kit according to claim 16, additionally comprising a vial containing a chromogenic substrate capable of reacting with said enzyme-labeled probe reagent to provide visible color.

19. An assay kit according to claim 18, wherein said chromogenic substrate is selected from the group consisting of: ABTS; TMB; DAB; and OPD.

20. An assay kit according to claim 16, wherein said target substance is an immunoglobulin and said immunoglobulin is derived, at least in part, from a non-human source, and said enzyme-labeled probe is derived, at least in part, from the same non-human source.

21. An immunoassay kit according to claim 16, additionally comprising a color gradient chart for comparison with visible color produced in patient test regions.

22. A method for detecting the presence of antibodies in a patient test specimen capable of binding to a diagnostic or therapeutic substance proposed for in vivo administration to the patient, comprising sequentially:

contacting a plurality of patient specimen test regions corresponding to a plurality of densities of a target substance with the patient test specimen for an antibody binding incubation period, wherein said target substance has binding characteristics similar to binding characteristics of the diagnostic or therapeutic substance proposed for in vivo administration;

removing unbound constituents of the patient test specimen from said patient specimen test regions;

contacting said plurality of patient specimen test regions with a labeled probe reagent capable of binding to antibody immobilized on said plurality of patient specimen test regions for a a labeled probe binding incubation period;

removing unbound constituents of said labeled probe reagent; and determining the quantity of said labeled probe at each said patient specimen test region.

23. A method according to claim 22, wherein said labeled probe comprises an enzyme-labeled probe, and said method additionally comprises contacting said plurality of patient specimen test regions with a chromogenic substrate capable of reacting with said enzyme-labeled probe, and removing constituents of said chromogenic substrate which have not reacted with said enzyme-labeled probe prior to determining the quantity of said labeled probe at each said patient specimen test region.

24. A method according to claim 22, wherein said target substance is a target immunoglobulin and has binding characteristics similar to a carrier moiety of an immunoconjugate proposed for in vivo administration.

25. A method according to claim 24, wherein said target immunoglobulin is functionally equivalent to said carrier moiety.

26. A method according to claim 25, wherein specificity determining regions of said target immunoglobulin are identical to corresponding specificity determining regions of said carrier moiety.

27. A method according to claim 24, wherein said target immunoglobulin and said carrier moiety are derived, at least in part, from the same species of origin.

28. A method according to claim 22, wherein said target substance has binding characteristics similar to an effector moiety of an immunoconjugate proposed for in vivo administration.

* * * * *

UNITED STATES PATENT AND TRADEMARK OFFICE

CERTIFICATE OF CORRECTION

PATENT NO. : 4,968,604

DATED : November 6, 1990

INVENTOR(S) : Beatty

It is certified that error appears in the above-identified patent and that said Letters Patent is hereby corrected as shown below:

In column 10, line 24 [claim 1], please change "bas" to --has--.

In column 11, line 23 [claim 17], please change "comprise" to --comprises--.

Signed and Sealed this

Seventh Day of November, 1995

Attest:

BRUCE LEHMAN

*Attesting Officer*     *Commissioner of Patents and Trademarks*